(12) United States Patent
Castillo

(10) Patent No.: US 7,182,740 B1
(45) Date of Patent: Feb. 27, 2007

(54) ONE PIECE BRACE LINER HAVING MULTIPLE ADJUSTMENT ZONES

(75) Inventor: David Castillo, Mission Viejo, CA (US)

(73) Assignee: Asterisk.Asterisk, LLC, Lake Forest, CA (US)

( * ) Notice: Subject to any disclaimer, the term of this patent is extended or adjusted under 35 U.S.C. 154(b) by 0 days.

(21) Appl. No.: 11/441,951

(22) Filed: May 26, 2006

(51) Int. Cl.
*A61F 5/00* (2006.01)

(52) U.S. Cl. .............................. 602/5; 602/26; 602/21; 602/22

(58) Field of Classification Search ............... 602/5, 602/16, 23, 26, 61–63; 128/882; 5/624, 5/648, 650, 22, 911
See application file for complete search history.

(56) References Cited

U.S. PATENT DOCUMENTS

| | | | | |
|---|---|---|---|---|
| 4,805,606 A | * | 2/1989 | McDavid, III | ............... 602/26 |
| 5,599,288 A | * | 2/1997 | Shirley et al. | ................ 602/26 |
| 7,122,016 B1 | * | 10/2006 | DeToro et al. | ................ 602/26 |

* cited by examiner

*Primary Examiner*—Teena Mitchell
*Assistant Examiner*—Kristen C. Matter
(74) *Attorney, Agent, or Firm*—Stetina Brunda Garred & Brucker

(57) ABSTRACT

A joint protecting brace includes a cuff member. The cuff member includes a pair of upper lateral and lower lateral tightening portions positioned on opposed sides of a cuff longitudinal axis. The cuff member further includes a liner disposed between and coupled to the upper lateral tightening portions and lower lateral tightening portions and extending along the cuff longitudinal axis. The cuff member further includes a connector coupled to a latitudinal strap. The cuff member further includes a first adjuster coupled to the upper lateral tightening portions and the connector. The cuff member further includes a second adjuster coupled to the lower lateral tightening portions and the connector. The first and second adjusters are disposed in tension for adjusting a distance between the upper and lower lateral tightening portions respectively. The first and second adjusters are communicable via the connector.

9 Claims, 4 Drawing Sheets

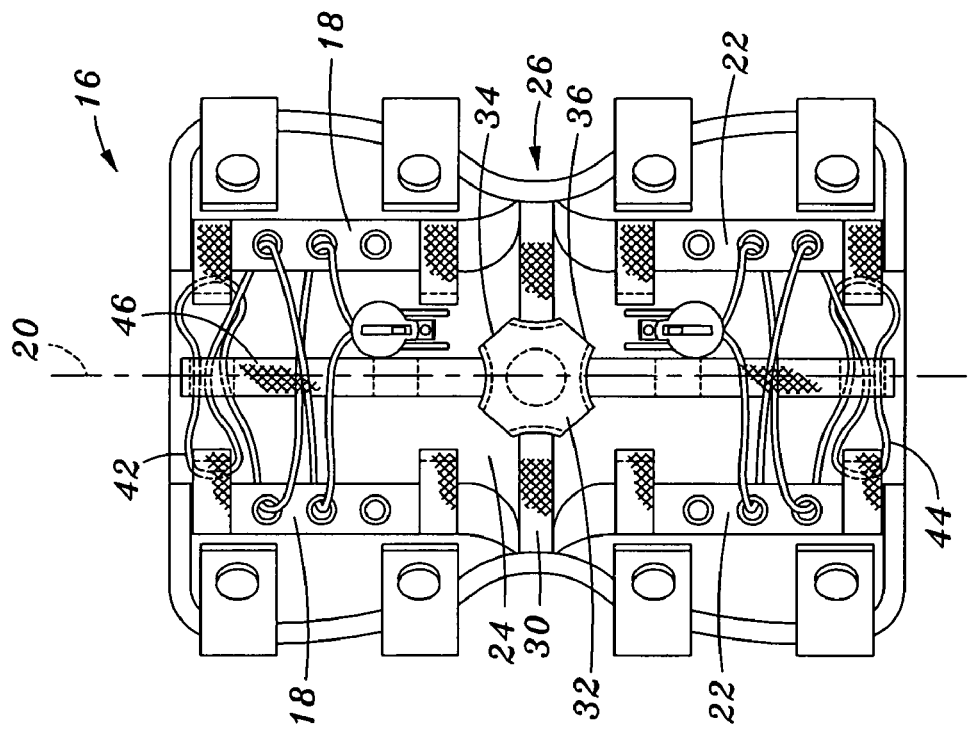
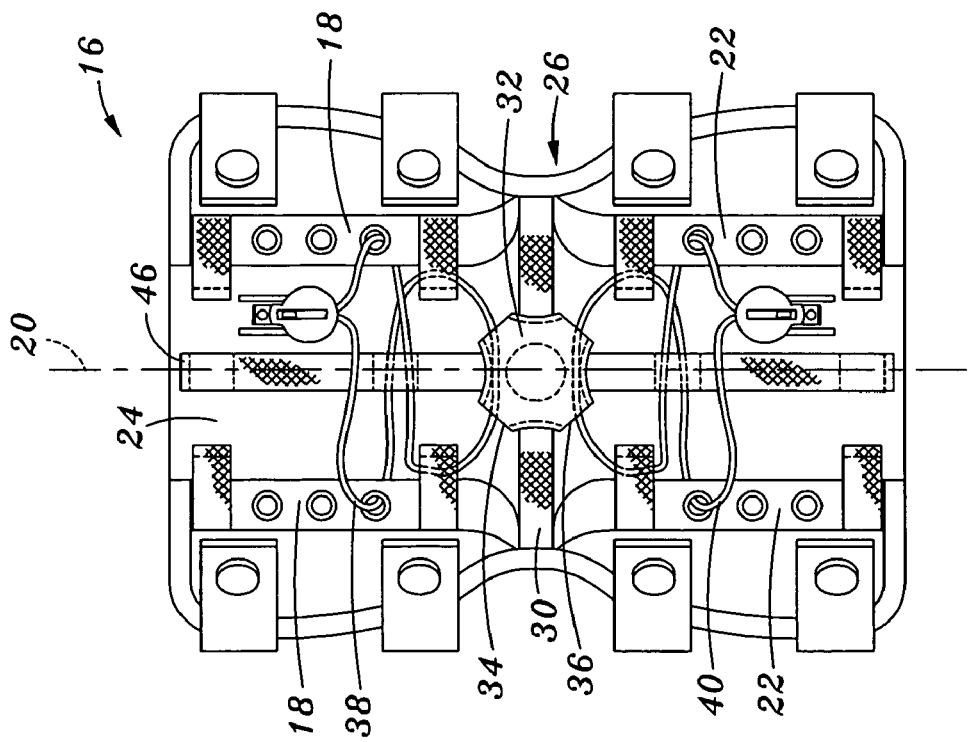

ONE PIECE BRACE LINER HAVING MULTIPLE ADJUSTMENT ZONES

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Field of Invention

This invention relates in general to an exteriorly positional anatomical brace for stabilizing a pivoting joint. Specifically, the brace includes a cuff having multiple adjustment zones allowing a user to tighten or loosen the brace. The brace prevents hyperextension of joint ligaments by communicating the movement of a first limb structure to a second limb structure.

2. Description

The health and well-being of all joints in the human body are susceptible to disease and injury. The human body contains many joints throughout the body; however one joint in particular is very susceptible to injury, namely, the knee joint. The knee joint is located on a leg and connects the femur to the tibia. Other bones surrounding the knee joint include the patella and the fibula. The bones of the knee joint are held together by four ligaments, namely the anterior cruciate ligament, posterior cruciate ligament, medial collateral ligament, and lateral collateral ligament. An injury to the knee involves a strain or tear in any of the above-mentioned ligaments.

An injury to the knee joint may occur during normal, everyday activity. A simple misstep or twist in the wrong direction could strain or tear a ligament. However, injury is more likely to occur during sports related activities. During such activities, large forces may be applied to the joint, thereby causing a strain or tear in one or more of the ligaments. For example, in football, as players are tackled, a player may sustain a hit directly to his knee; in basketball, players apply forces to their knees when they routinely change their direction by planting their foot and quickly changing their course. However, one sport that can particularly cause considerable injury to a knee is motocross. In motocross, a rider's knee acts as a shock absorber as the rider traverses over a course's rough terrain by landing large jumps, or maneuvering through a series of bumps. In addition to acting as a shock absorber, a rider's knee is susceptible to sudden twists which can cause injury. For instance, as a rider moves through the course, his foot may get caught in the dirt, thereby twisting the rider's knee.

Whatever the activity may be, one can mitigate the chance of injuring a joint by fitting a brace around the joint. Athletes have been protecting their knees by wearing knee braces for years. A knee brace protects the knee joint by stabilizing the bones surrounding the knee. By stabilizing the movement of the bones, the changes of straining or tearing a ligament is lessened.

In the related art, most braces include an upper frame member attached to a first limb structure and a lower frame member attached to a second limb structure. Each frame member typically includes an adjustable cuff positionable on a concave surface of the joint. The cuff can be tightened to secure the frame member to its respective limb structure.

Despite the protection offered by most braces, injuries to joints continue to occur. A number of injuries occur because of the lack of protection on the concave surface of the joint. Chief among such injuries are hyperextensions of the knee ligaments. Hyperextensions continue to occur despite the presence of a knee brace because of the lack of support and stabilization on the concave surface of the joint. The typical knee brace does not stabilize the rearward movement of the first limb structure relative to the second limb structure. As such, there is a need in the art for an improved knee brace that prevents hyperextension of the joint by preventing the rearward movement of the first and second limb structures relative to each other.

BRIEF SUMMARY

According to an aspect of the present invention there is provided an exteriorly positional anatomical brace for stabilizing a pivoting joint. The joint is disposed between a first limb structure and a second limb structure of a living being. The pivoting joint includes a concave surface.

The brace includes an upper frame member positionable adjacent the first limb structure and a lower frame member positionable adjacent the second limb structure. The brace further includes a joint member pivotally connecting the upper frame member and the lower frame member. The brace also includes a cuff member. The cuff member includes a pair of upper lateral tightening portions positioned on opposed sides of a cuff longitudinal axis. The upper lateral tightening portions are attached to the upper frame member. The cuff member further includes a pair of lower lateral tightening portions positioned on opposed sides of the cuff longitudinal axis. The lower lateral tightening portions are attached to the lower frame member. The cuff member further includes a liner extending along the cuff longitudinal axis. The liner is disposed between and coupled to the upper lateral tightening portions. The liner is also disposed between and coupled to the lower lateral tightening portions. The liner includes a bend region positionable adjacent the concave surface of the joint. The bend region is located between upper and lower lateral tightening portions. The cuff member further includes a latitudinal strap positioned along the bend region, and a connector coupled to the latitudinal strap. The connector includes a top region and a bottom region. The cuff member further includes a first adjuster coupled to the upper lateral tightening portions and the top region of the connector. The first adjuster is disposed in tension for adjusting a first distance between the upper lateral tightening portions. The cuff member further includes a second adjuster coupled to the lower lateral tightening portions and the bottom region of the connector. The second adjuster is disposed in tension for adjusting a first distance between the lower lateral tightening portions. The first and second adjusters are communicable via the connector.

In operation, the brace is secured to the user such that the upper frame member is positioned adjacent the first limb structure, the lower frame member is positioned adjacent the second limb structure, and the liner is positioned adjacent the concave surface of the joint. The first adjuster is disposed in tension thereby decreasing the distance between the pair of upper lateral tightening portions and increasing the pressure applied by the cuff member to the first limb structure. The second adjuster is additionally disposed in tension, thereby decreasing the distance between the pair of lower lateral tightening portions and increasing the pressure applied by the cuff member to the second limb structure. The first and second adjusters are communicable via the connector member. Therefore, as the tension in the first adjuster increases, the tension in the second adjuster also increases. Likewise, as the tension in the second adjuster increases, the tension in the first adjuster also increases. Such communicability links the movement of the first limb structure to the movement of the second limb structure, thereby reducing the risk of injury to the joint.

According to various embodiments of the invention, the cuff member may include a third adjuster coupled to the upper lateral tightening portions. The third adjuster may be disposed in tension for adjusting a second distance between the upper lateral tightening portions. The cuff member may further include a fourth adjuster coupled to the lower lateral tightening portions. The fourth adjuster may be disposed in tension for adjusting a second distance between the lower lateral tightening portions. In such embodiments including first, second, third and fourth adjusters, the cuff member will be considered to have four zones of adjustment. Each adjuster is considered to control one zone of adjustment.

The cuff member may further include a longitudinal strap coupled to the liner. The longitudinal strap may be positioned along the longitudinal axis. The connector may be coupled to the longitudinal strap to position the connector adjacent the liner.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 4 is an elevation view of a cuff member with first and second adjusters shown coupled to upper and lower lateral tightening portions, respectively, and the first and second adjusters being communicable via a connector member;

FIG. 5 is an elevation view of the cuff member of FIG. 4 with third and fourth adjusters shown coupled to the upper and lower lateral tightening portions, respectively;

DETAILED DESCRIPTION

An aspect of the present invention is a device designed to protect a joint of a user. Such a joint is located between a first limb structure and a second limb structure of the user. The device is intended to be secured to the first and second limb structures. The device protects the joint by stabilizing the movement of the first and second limb structures.

Figure 1:
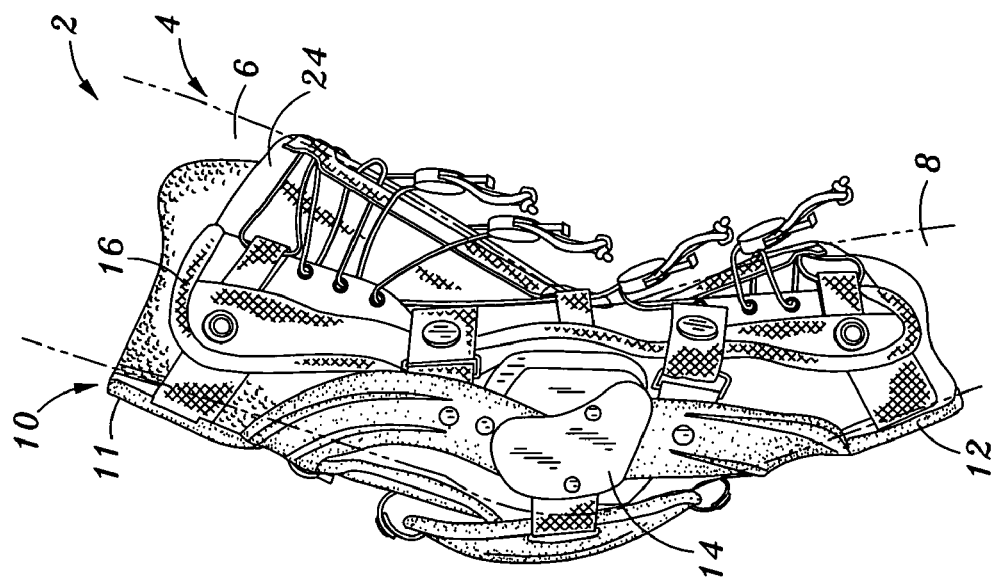
FIG. 1 is a perspective lateral view of an exteriorly positional anatomical brace having a cuff member, the brace positioned on a leg of a user shown in phantom.
Figure 2:
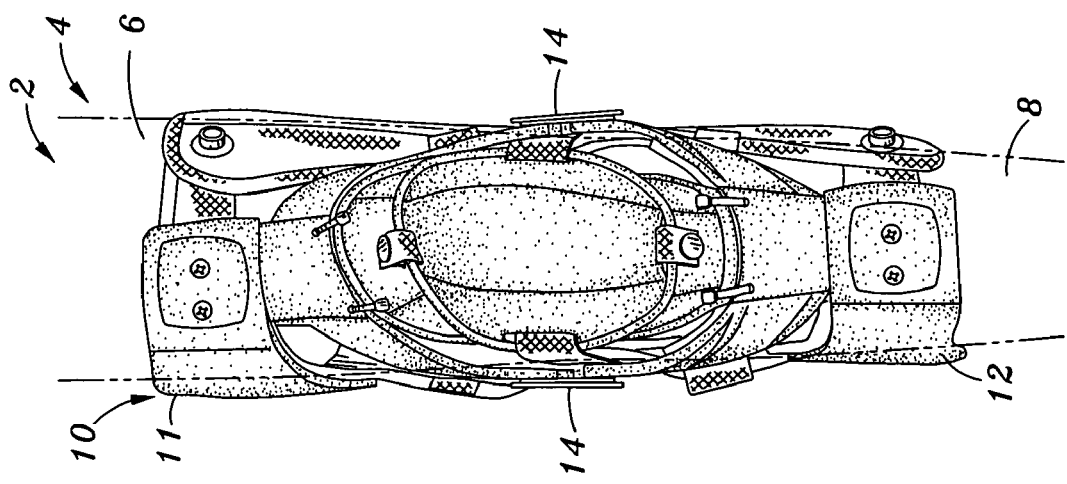
FIG. 2 is a perspective front view of the brace.
Figure 3:
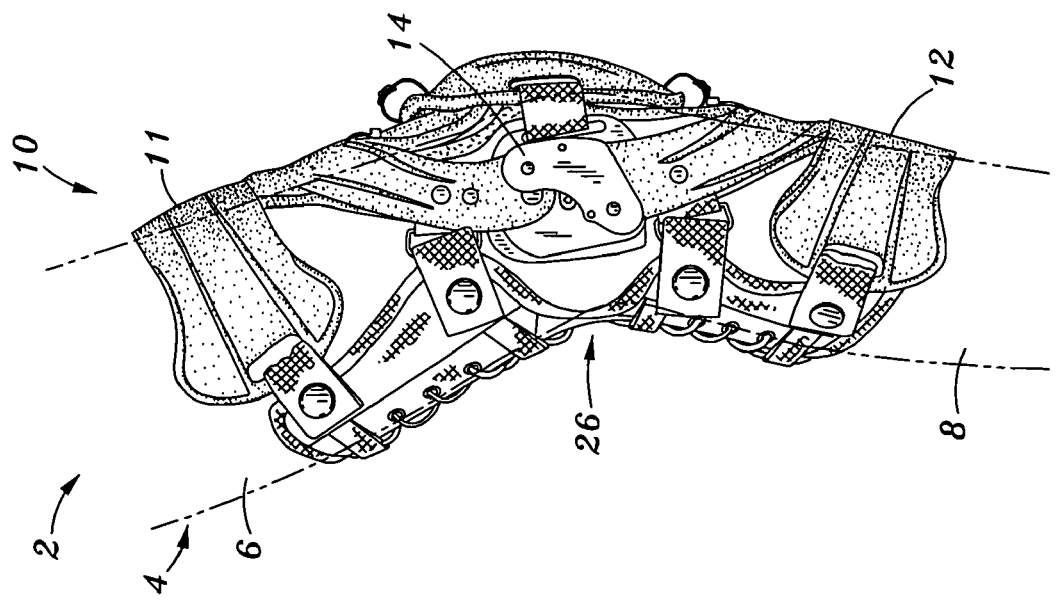
FIG. 3 is a perspective medial view of the brace without adjusters.

Referring to FIGS. 1–3, an exteriorly positional anatomical brace 10 is shown in place on a user 2. In the embodiment illustrated in FIGS. 1–3, the device is shown on a knee of the user 2, where the first limb structure 6 is an upper leg and the second limb structure 8 is a lower leg.

The brace 10 includes an upper frame member 11 positionable adjacent the first limb structure 6 of the user 2 and a lower frame member 12 positionable adjacent the second limb structure 8 of the user 2. The brace 10 further includes a joint member 14 pivotally connecting the upper frame member 11 and the lower frame member 12. The brace 10 also includes a cuff member 16. The cuff member 16 includes a pair of upper lateral tightening portions 18 positioned on opposed sides of a cuff longitudinal axis 20. The upper lateral tightening portions 18 attach to the upper frame member 11. The cuff member 16 further includes a pair of lower lateral tightening portions 22 positioned on opposed sides of the cuff longitudinal axis 20. The lower lateral tightening portions 22 attach to the lower frame member 12. The cuff member 16 further includes a liner 24 extending along the cuff longitudinal axis 20. The liner 24 is disposed between and coupled to the upper lateral tightening portions 18. The liner 24 is also disposed between and coupled to the lower lateral tightening portions 22. The liner 24 includes a bend region 26 positionable adjacent the concave surface of the joint. The bend region 26 is located between upper and lower lateral tightening portions 18, 22. The cuff member 16 further includes a latitudinal strap 30 positioned along the bend region 26 of the liner 24. The cuff member 16 further includes a connector 32 coupled to the latitudinal strap 30. The connector 32 includes a top region 34 and a bottom region 36. The cuff member 16 further includes a first adjuster 38 coupled to the upper lateral tightening portions 18 and the top region 34 of the connector 32. The first adjuster 38 is disposed in tension for adjusting a first distance between the upper lateral tightening portions 18. The cuff member 16 further includes a second adjuster 40 coupled to the lower lateral tightening portions 22 and the bottom region 36 of the connector 32. The second adjuster 40 is disposed in tension for adjusting a first distance between the lower lateral tightening portions 22. The first and second adjusters 38, 40 are communicable via the connector 32.

As described above, the upper and lower frame members 11, 12 are positionable adjacent the first and second limb structures 6, 8, respectively. In this regard, the upper and lower frame members 11, 12 are positioned near or close to the first and second limb structures 6, 8, but not necessarily touching the limb structures 6, 8. The upper frame member 11 is pivotally connected to the lower frame member 12 via the joint member 14. In this regard, the upper and lower frame members 11, 12 connect to the joint member 14 such that the upper frame member 11 and the lower frame member 12 rotate about the joint member 14.

FIGS. 1 and 3 show the cuff member 16 attached to the upper and lower frame members 11, 12. The cuff member 16 includes upper and lower lateral tightening portions 18, 22. The upper and lower lateral tightening portions 18, 22 attach to the upper and lower frame members 11, 12, respectively. Such attachment is preferably a detachable attachment, such as a snap fastener, or a hook and loop fastener. However, the upper and lower lateral tightening portions 18, 22 may be permanently attached to the upper and lower frame members 11, 12 using permanent attachment devices such as a rivet or screw.

FIGS. 4 and 5 show the cuff member 16 having a pair of upper and lower lateral tightening portions 18, 22. The pair of upper lateral tightening portions 18 are positioned on opposed sides of the cuff longitudinal axis 20. In this regard, an upper lateral tightening portion 18 is located on either side of the cuff longitudinal axis 20. The pair of lower lateral tightening portions 22 are also positioned on opposed sides of the cuff longitudinal axis 20. As such, a lower lateral tightening portion 22 is located on either side of the cuff longitudinal axis 20. As shown in FIGS. 4 and 5, the pair of upper lateral tightening portions 18 are not integrally formed. The pair of lower lateral tightening portions 22 are also not integrally formed. However, the upper lateral tightening portions 18 and the lower lateral tightening portions 22 may be integrally formed without departing from the scope of the invention.

FIGS. 4 and 5 also show the liner 24 extending along the cuff longitudinal axis 20. Preferably, the liner 24 is comprised of an elastic material, capable of bending without losing its structural integrity. As mentioned above, the liner 24 is disposed between the pair of upper lateral tightening portions 18. In this regard, the liner 24 extends between the pair of upper lateral tightening portions 18. In addition, the liner 24 is also disposed between the pair of lower lateral tightening portions 22. As such, the liner 24 extends between the pair of lower lateral tightening portions 22. The liner is coupled to the upper lateral tightening portions and the lower lateral tightening portions. Preferably, the liner 24 is sewn or stitched to the upper and lower lateral tightening portions 18, 22, thereby permanently coupling the liner 24 to the upper and lower lateral tightening portions 18, 22.

In the preferred embodiment of the invention, the cuff member 16 includes only one liner 24, as is shown in FIGS. 4 and 5. The liner 24 extends along the cuff longitudinal axis 20 from the lower frame member 11 to the upper frame member 12. As explained above, the liner 24 includes a bend region 26 located between the upper and lower lateral tightening portions 18, 22. The bend region 26 is positionable adjacent the concave surface of the joint. In this regard, the bend region 26 is situated next to or near the concave surface of the joint. The bend region 26 does not necessarily have to be in contact with the concave surface of the joint.

The cuff member 16 having a connector 32. As mentioned above, the connector 32 is coupled to the latitudinal strap 30. In this regard, the connector 32 is fixedly coupled to the latitudinal strap 30 by being stitched or sewn to the strap 30. However, the connector 32 may be detachably coupled to the strap 30 using snap fasteners or hook and loop fasteners. The latitudinal strap 30 holds the connector 32 in place, adjacent to the liner 24, as the brace 10 is in use.

FIG. 4 shows the cuff member 16 having first and second adjusters 38, 40. Preferably the first and second adjusters 38, 40 are comprised of a non-elastomeric lace. As described above, the first adjuster 38 is coupled to the upper lateral tightening portions 18 and the top region 34 of the connector 32. The second adjuster 40 is coupled to the lower lateral tightening portions 22 and the bottom region 36 of the connector 32. The top region 34 of the connector 32 is the region through which the first adjuster 38 passes through. The bottom region 36 of the connector 32 is the region through which the second adjuster 40 passes through. As shown in FIG. 4, the upper and lower lateral tightening portions 18, 22 are provided with eyelets which the first and second adjusters 38, 40 are laced through.

The first adjuster 38 is disposed in tension for adjusting a first distance between the upper lateral tightening portions 18. In this regard, as the user 2 increases the tension in the first adjuster 38, the distance between the upper lateral tightening portions 18 decreases, thereby increasing the pressure applied by the cuff member 16 to the first limb structure 6. Likewise, the second adjuster 40 is disposed in tension for adjusting a first distance between the lower lateral tightening portions 22. As the user 2 increases the tension in the second adjuster 40, the distance between the lower lateral tightening portions 22 decreases, thereby increasing the pressure applied by the cuff member 16 to the second limb structure 8.

The tensions of the first and second adjusters 38, 40 are communicable via the connector 32. The tensions of the first and second adjusters 38, 40 fluctuate as the user 2 moves his first and second limb structures 6, 8. The tension in the first or second adjusters 38, 40 increases when one of the first or second limb structures 6, 8 begins to separate or extend from its natural position in the joint. A hyperextension of the joint occurs when one of the first or second limb structures 6, 8 separates from its natural position so as to strain or tear the ligaments securing the joint. An increase in tension in one of the first or second adjusters 38, 40, is communicated to the other one of the first or second adjusters 38, 40 via the connector 32. By communicating the increase in tension in one of the first or second adjusters 38, 40 to the other one of the first or second adjusters 38, 40 the pressure of the entire cuff member 16, as applied to the first and second limb structures 6, 8 increases. The increase in pressure of the cuff member 16 as applied to the first and second limb structures 6, 8 stabilizes the joint thereby decreasing the chances of hyperextending the joint.

Figure 7:
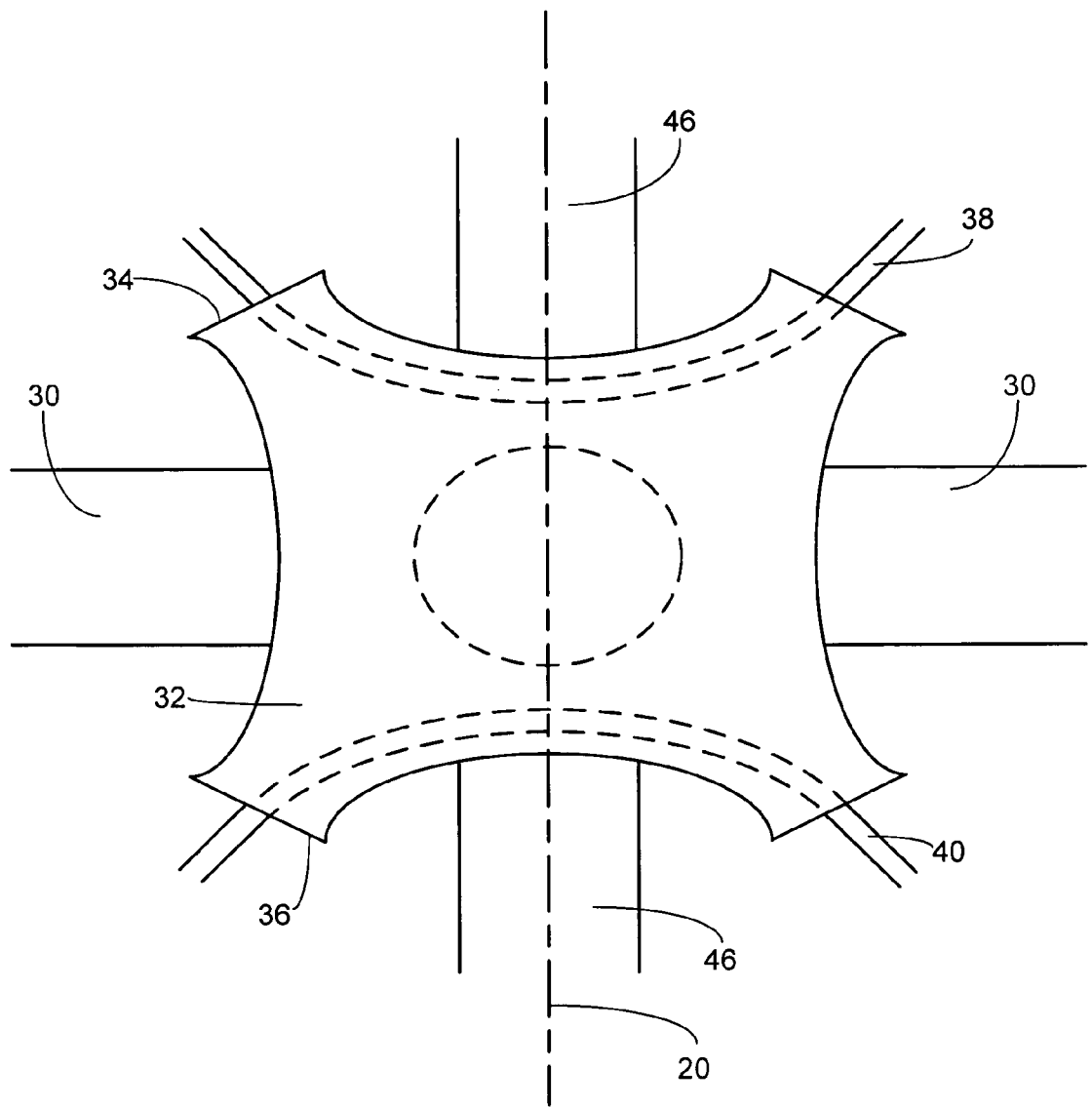
FIG. 7 is a perspective view of the connector.

FIG. 7 shows a perspective view of the connector 32. Preferably, the connector 32 guides the first adjuster 38 such that when the first adjuster 38 is disposed in tension, the portions of the first adjuster 38 exiting the top region 34 of the connector 32 are directed in non-parallel directions. Likewise, the connector 32 guides the second adjuster 40 such that when the second adjuster 40 is disposed in tension, the portions of the second adjuster 40 exiting the bottom region 36 of the connector 32 are directed in non-parallel directions. Therefore, as the tension increases in any of the directions of one of the first or second adjusters 38, 40, such increase in tension is communicated to the other one of the first or second adjusters 38, 40.

The cuff member 16 may also include a third adjuster 42 and a fourth adjuster 44. FIG. 5 shows a view of the cuff member 16 having third and fourth adjusters 42, 44. Preferably, the third and fourth adjusters 42, 44 will be used in addition to the first and second adjusters 38, 40. The third adjuster 42 is coupled to the pair of upper lateral tightening portions 18. The third adjuster 42 is disposed in tension for adjusting a second distance between the upper lateral tightening portions 18. Similarly, the fourth adjuster 44 is coupled to the pair of lower lateral tightening portions 22. The fourth adjuster 44 is disposed in tension for adjusting a second distance between the lower lateral tightening portions 22.

Figure 6:
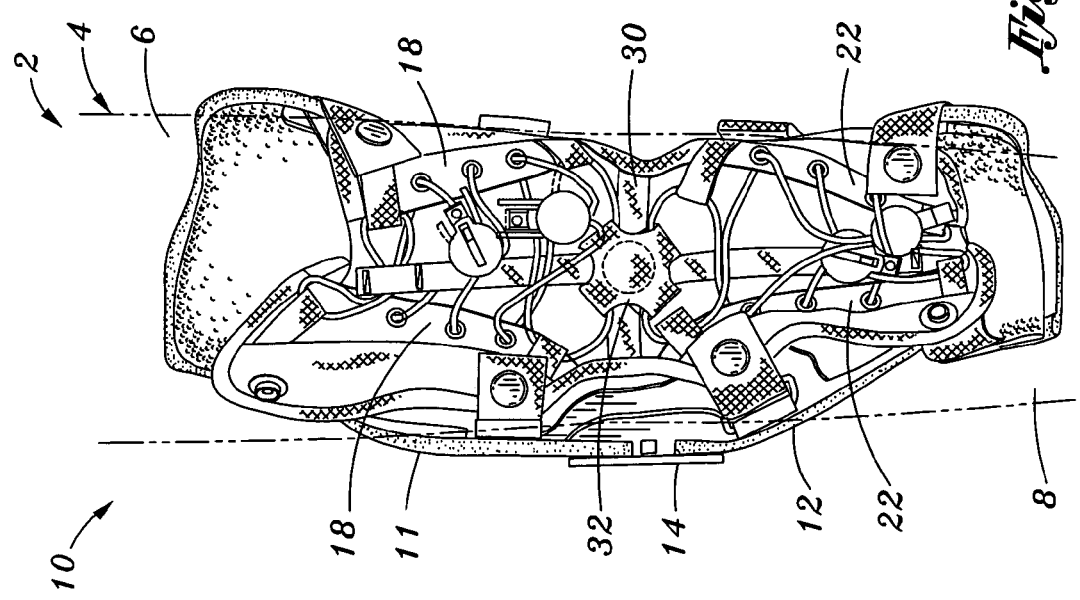
FIG. 6 is a perspective rear view of the brace of FIG. 1 having first, second, third and fourth adjusters.

According to an aspect of the present invention, a user 2 is able to tighten or loosen the brace 10 by adjusting the tension in the adjusters 38, 40, 42, 44. Each adjuster 38, 40, 42, 44 controls one zone of adjustment. Preferably, the brace 10 includes multiple zones of adjustment. FIG. 6 is a perspective rear view of the brace 10 having first, second, third and fourth adjusters 38, 40, 42, 44. In such an embodiment, the brace 10 has four zones of adjustment; two control the upper lateral tightening portions 18, while two control the lower lateral tightening portions 22.

The adjusters 38, 40, 42, 44 must be capable of being disposed in tension. The preferred material for the adjusters 38, 40, 42, 44 is a non-elastomeric lace, or other appropriate materials as would be recognized by the skilled artisan.

FIGS. 4–5 shows an alternative embodiment of the brace 10 containing a longitudinal strap 46. The longitudinal strap 46 is coupled to the liner 24 and positioned along the cuff longitudinal axis 20. The longitudinal strap 46 connects the liner 24 to the connector 32. Therefore, as the liner 24 expands or stretches the connector 32 moves accordingly.

In operation, a user 2 secures the brace 10 to the first and second limb structures 6, 8. As shown in FIGS. 1, 2 and 3, the user 2 secures the brace 10 to the leg 4 of a user 2. The brace 10 is secured to the user 2 by positioning the upper frame member 11 adjacent the first limb structure 6 and positioning the lower frame member 12 adjacent the second limb structure 8. A cuff member 16 is attached to the upper and lower frame members 18, 22. The cuff member 16 is positioned such that the bend region 26 of the liner 24 is adjacent the concave surface of the joint of the user 2. The user 2 adjusts a first distance between the pair of upper lateral tightening portions 18 by disposing the first adjuster 38 in tension. The user 2 also adjusts a first distance between the pair of lower lateral tightening portions 22 by disposing the second adjuster 40 in tension. A connector 32 communicates the tensile forces of the first adjuster 38 with the tensile forces of the second adjuster 40.

The brace 10 may also include third and fourth adjusters 42, 44. A user 2 may adjust a second distance between the pair of upper lateral tightening portions 18 using the third adjuster 42. Similarly, a user 2 may adjust a second distance between the pair of lower lateral tightening portions 22 using the fourth adjuster 44.

The increase in tension in the adjusters 38, 40, 42, 44 increases the pressure applied by the cuff member 16 to the first and second limb structures 6, 8. As the tension in one of the first or second adjusters 38, 40 increases, the connector 32 communicates the increase in tension to the other one of the first and second adjusters 38, 40. The tension in the other one of the first or second adjusters 38, 40 is thereby increased. The increase in tension stabilizes the joint and prevents hyperextension.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. An exteriorly positional anatomical brace for stabilizing a pivoting joint, the joint being disposed between a first limb structure and a second limb structure of a living being, the joint having a concave surface, the brace comprising:
    an upper frame member positionable adjacent the first limb structure;
    a lower frame member positionable adjacent the second limb structure;
    a joint member pivotally connecting the upper frame member and the lower frame member; and
    a cuff member including:
        a pair of upper lateral tightening portions positioned on opposed sides of a cuff longitudinal axis, the upper lateral tightening portions being attached to the upper frame member;
        a pair of lower lateral tightening portions positioned on opposed sides of the cuff longitudinal axis, the lower lateral tightening portions being attached to the lower frame member;
        a liner extending along the cuff longitudinal axis, the liner disposed between and coupled to the upper lateral tightening portions, the liner disposed between and coupled to the lower lateral tightening portions, the liner having a bend region positionable adjacent the concave surface of the joint, the bend region located between upper and lower lateral tightening portions;
        a latitudinal strap positioned along the bend region;
        a connector coupled to the latitudinal strap, the connector having a top region and a bottom region;
        a first adjuster coupled to the upper lateral tightening portions and the top region of the connector, the first adjuster being disposed in tension for adjusting a first distance between the upper lateral tightening portions; and
        a second adjuster coupled the lower lateral tightening portions and the bottom region of the connector, the second adjuster being disposed in tension for adjusting a first distance between the lower lateral tightening portions, the first and second adjusters being communicable via the connector.

2. The brace of claim 1, wherein the cuff member is further comprised of a third adjuster coupled to the upper lateral tightening portions, the third adjuster being disposed in tension for adjusting a second distance between the upper lateral tightening portions.

3. The brace of claim 2, wherein the third adjuster is comprised of non-elastomeric lace.

4. The brace of claim 2, wherein the cuff member is further comprised of a fourth adjuster coupled to the lower lateral tightening portions, the fourth adjuster being disposed in tension for adjusting a second distance between the lower lateral tightening portions.

5. The brace of claim 4, wherein the fourth adjuster is comprised of non-elastomeric lace.

6. The brace of claim 1, wherein the cuff member is further comprised of a longitudinal strap coupled to the liner, the longitudinal strap being positioned along the longitudinal axis.

7. The brace of claim 1, wherein the liner is comprised of an elastic material.

8. The brace of claim 1, wherein the first adjuster is comprised of non-elastomeric lace.

9. The brace of claim 1, wherein the second adjuster is comprised of non-elastomeric lace.

* * * * *